(12) United States Patent
Ye et al.

(10) Patent No.: US 12,370,093 B2
(45) Date of Patent: Jul. 29, 2025

(54) SELF-ADHESIVE SANITARY PRODUCT AND PREPARATION METHOD THEREOF

(71) Applicant: Tsinghua University, Beijing (CN)

(72) Inventors: Yilan Ye, Beijing (CN); Zhenzhong Yang, Beijing (CN)

(73) Assignee: Tsinghua University, Beijing (CN)

( * ) Notice: Subject to any disclaimer, the term of this patent is extended or adjusted under 35 U.S.C. 154(b) by 413 days.

(21) Appl. No.: 18/048,093

(22) Filed: Oct. 20, 2022

(65) Prior Publication Data

US 2023/0320909 A1    Oct. 12, 2023

(30) Foreign Application Priority Data

Apr. 12, 2022   (CN) .......................... 202210382933.6

(51) Int. Cl.
| | | |
|---|---|---|
| *A61F 13/47* | (2006.01) | |
| *A61L 15/22* | (2006.01) | |
| *A61L 15/28* | (2006.01) | |
| *A61L 15/32* | (2006.01) | |
| *A61L 15/58* | (2006.01) | |
| *C08L 1/04* | (2006.01) | |

(Continued)

(52) U.S. Cl.
CPC ............ *A61F 13/47* (2013.01); *A61L 15/225* (2013.01); *A61L 15/28* (2013.01); *A61L 15/32* (2013.01); *A61L 15/58* (2013.01); *C08L 1/04* (2013.01); *C08L 5/04* (2013.01); *C08L 5/08* (2013.01); *C08L 75/04* (2013.01)

(58) Field of Classification Search
CPC ...... A61F 13/47; A61F 13/2085; A61F 13/20; A61F 13/2002; A61F 13/202; A61F 13/2022; A61F 13/2071; A61F 6/06; A61F 6/065; A61F 6/08; A61F 5/4553
See application file for complete search history.

(56) References Cited

U.S. PATENT DOCUMENTS

| | | | |
|---|---|---|---|
| 4,198,965 A | * | 4/1980 | Strickman ............ A61K 9/0036 128/832 |
| 5,927,282 A | | 7/1999 | Lenker et al. |

FOREIGN PATENT DOCUMENTS

| | | |
|---|---|---|
| CN | 2260593 Y | 8/1997 |
| CN | 202211778 U | 5/2012 |

(Continued)

*Primary Examiner* — Susan S Su
*Assistant Examiner* — Erin A Kim
(74) *Attorney, Agent, or Firm* — Grossman, Tucker, Perreault & Pfleger, PLLC

(57) ABSTRACT

The disclosure relates to a self-adhesive sanitary product and a preparation method thereof. The product is fingerstall-like or sheet-like, and has a first face on a surface side and a second face on the opposite side of the first face. On the first face, the product has a micro-nano array structure which can achieve reversible wet adhesion and which is configured to be adhered to a vaginal orifice tissue or a urethral orifice tissue. The self-adhesive sanitary product has air permeability and liquid impermeability. When the self-adhesive sanitary product is adhered to the vaginal orifice tissue or the urethral orifice tissue, the self-adhesive sanitary product completely blocks the vaginal orifice or the urethral orifice to prevent contents of the vagina or the urethra from flowing out. The self-adhesive sanitary product according to the present disclosure has the advantages of safety, comfort, privacy, miniature, environmental protection, affordability and the like.

13 Claims, 3 Drawing Sheets

(51) Int. Cl.
*C08L 5/04* (2006.01)
*C08L 5/08* (2006.01)
*C08L 75/04* (2006.01)

(56) References Cited

FOREIGN PATENT DOCUMENTS

| | | |
|---|---|---|
| CN | 105769416 A | 7/2016 |
| CN | 108175576 A | 6/2018 |
| CN | 210870003 U | 6/2020 |
| CN | 211095140 U | 7/2020 |
| JP | 5737680 B1 | 6/2015 |
| WO | 9211825 A1 | 7/1992 |

\* cited by examiner

SELF-ADHESIVE SANITARY PRODUCT AND PREPARATION METHOD THEREOF

TECHNICAL FIELD

The present disclosure relates to a sanitary product, in particular to a self-adhesive sanitary product.

BACKGROUND

At present, menstrual sanitary products and diapers for urinary incontinence generally have problems such as poor performance and environmental pollution. Women's menstrual sanitary products are divided into the following three categories: menstrual cups, sanitary napkins and tampons.
  (i). Menstrual cup: the main material is silicone and the shape is like a cup; during menstruation, the menstrual cup is squashed and inserted into the vagina, is taken out every 4 to 12 hours to remove the menstrual blood from the cup, and then is put back into the vagina to continue to hold the menstrual blood; when a menstrual period ends, the menstrual cup is cleaned and boiled with boiling water, and dried for later use; and, although the menstrual cup can be used repeatedly, it is inconvenient to operate and is not comfortable to use, and moreover special attention have to be paid to disinfection and sterilization, so few people choose to use the menstrual cup.
  (ii). Sanitary napkin: the main material is polymeric water-absorbent resin, which can absorb menstrual blood; during menstruation, the sanitary napkin is stuck on the inside of the underwear, and is changed for a new one for about 4 hours; since the sanitary napkin is convenient to use, it has many users; nevertheless, the sanitary napkin has some disadvantages, such as leakage, less comfort, and that it can't be used during swimming; the sanitary napkin is a disposable product, which cannot be recycled after being polluted by menstrual blood and thus pollutes the environment; and moreover, the price of sanitary napkins is high, and there have been problems such as "menstrual poverty" in the society.
  (iii). Tampon: the main materials are cotton fiber and adhesive fiber, which can absorb menstrual blood; during menstruation, the tampon is inserted into the vagina and changed flexibly; the tampon does not make it inconvenient for exercise, but it is inconvenient to operate and provides less comfort, so it has few users; and furthermore, the tampon is also a disposable product, which cannot be recycled after being contaminated by menstrual blood and thus pollutes the environment.

For patients suffering from urinary incontinence, diapers need to be used frequently, which will cause environmental pollution. For some families, frequent replacement of diapers will also lead to unbearable expenses.

SUMMARY

The present disclosure aims to provide a self-adhesive sanitary product with the advantages of being safe, comfortable, private, miniature, environmentally friendly, affordable, and its preparation method.

Some embodiments of the present disclosure provide a self-adhesive sanitary product, wherein
  the self-adhesive sanitary product is fingerstall-like or sheet-like, and has a first face on a surface side and a second face on an opposite side of the first face,
  the self-adhesive sanitary product, on the first face, has a micro-nano array structure configured to achieve reversible wet adhesion and configured to be adhered to a vaginal orifice tissue or a urethral orifice tissue, and
  the self-adhesive sanitary product has air permeability and liquid impermeability, and when the self-adhesive sanitary product is adhered to the vaginal orifice tissue or the urethral orifice tissue, the self-adhesive sanitary product completely blocks the vaginal orifice or the urethral orifice to prevent contents of the vagina or the urethra from flowing out.

Optionally, the self-adhesive sanitary product comprises a base layer and a surface adhesive layer, wherein the base layer provides mechanical support for the surface adhesive layer, and the surface adhesive layer has the micro-nano array structure on the first face.

Optionally, the micro-nano array structure comprises an octopus-like structure provided with a plurality of suckers, an outer diameter of the sucker being 20 to 500 µm, an inner diameter of the sucker being 10 to 300 µm, a height of the sucker being 10 to 200 µm, and a distance between the outer diameters of the adjacent suckers being 0.5 to 2 times of the inner diameter of the sucker.
  the outer diameter of the sucker is 100 to 200 µm, the inner diameter of the sucker is 50 to 150 µm, and the height of the sucker is 30 to 100 µm.

Optionally, a wet adhesion strength of the self-adhesive sanitary product is 10 to 100 kPa.

Optionally, the fingerstall-like self-adhesive sanitary product has a thickness of 0.1 to 0.5 mm, a length of 1 to 3 cm, and an open end with a diameter of 1.2 to 2 cm; and
  the sheet-like self-adhesive sanitary product has a thickness of 0.1 to 0.5 mm, and a size that completely blocks the vaginal orifice or the urethral orifice.

Optionally, a thickness of the base layer is 90 to 300 µm, a thickness of the surface adhesive layer is 10 to 200 µm, and the thickness of the base layer is larger than the thickness of the surface adhesive layer.

Optionally, a modulus of the self-adhesive sanitary product is 10 to 100 kPa, and a breaking stress of the self-adhesive sanitary product is 1 to 10 MPa.

Optionally, the first face of the self-adhesive sanitary product is provided with a drug-loaded slow-release layer, and after the self-adhesive sanitary product is adhered to the vaginal orifice tissue or the urethral orifice tissue, the drug is slowly released into the vagina or the urethra.

Optionally, at least a part of the sucker in a height direction is provided with an elastic folding portion, the elastic folding portion is in a natural stretch state without any external force and in a compressed and folded state under an external force.

Optionally, the micro-nano array structure further comprises a mechanical interlocking structure serving as a complementary structure which fits the first surface to a tissue surface of the vaginal orifice tissue or the urethral orifice tissue.

Optionally, material of the self-adhesive sanitary product includes one of, or a combination of some or all of sodium alginate, hyaluronic acid, carboxymethyl cellulose, xanthan gum, gellan gum, gelatin, chitosan, medical polyurethane, polyglycolic acid, polylactic acid, polylactic acid-ethanolic acid copolymer, or polycaprolactone.

Some embodiments of the present disclosure provide a preparation method of a self-adhesive sanitary product, comprising:

preparing a base layer: obtaining a sheet-like or fingerstall-like base layer film by 3D printing or electrostatic spinning or thermal pressing or ultraviolet curing;

preparing a surface adhesive layer: obtaining a sheet-like or fingerstall-like surface adhesive layer film by 3D printing or using a mold with a micro-nano array structure;

combining the surface adhesive layer with the base layer: bonding the sheet-like surface adhesive layer film with the sheet-like base layer film or boding fingerstall-like surface adhesive layer film with the fingerstall-like base layer film to obtain an interface adhesive element; and making the interface adhesive element into a sheet shape or a fingerstall shape with a predetermined size by cutting and/or bonding.

Figure 1:
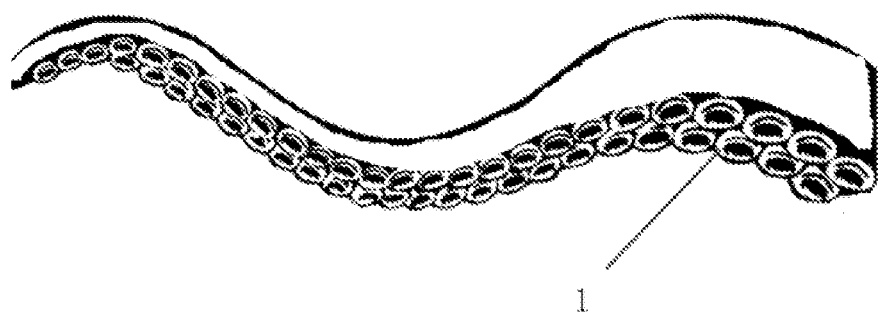
FIG. 1 is a schematic view of an octopus tentacle.

EXPLANATION OF THE REFERENCE NUMERALS 1. sucker of an octopus tentacle
2. self-adhesive sanitary product
3. vaginal orifice
4. surface adhesive layer
5. base layer
6. sucker
7. elastic folding portion

DETAILED DESCRIPTION OF THE EMBODIMENTS

The self-adhesive sanitary product according to embodiments of the present disclosure will be described below with reference to the accompanying drawings. It should be noted that the sizes of the respective components in the drawings may be inconsistent with their actual sizes, so it is necessary to take the actual situation into consideration. In addition, the embodiments described below are only examples serving to illustrate the present disclosure, and the present disclosure is not limited to them; and modifications, combinations, changes, etc. carried out within the scope of protection of the present disclosure are included in the present disclosure.

In view of the existing disadvantages of inconvenient operation, poor comfort, leakage, environmental pollution, and high selling prices of the women's menstrual sanitary products and the above problems caused by the use of diapers by patients suffering from urinary incontinence, embodiments of the present disclosure aim to provide a self-adhesive sanitary product with the advantages of being safe, comfortable, private, miniature, environmentally friendly, affordable, etc. and its preparation method.

First Embodiment

FIG. 1 shows an octopus tentacle on which there are a plurality of suckers 1. Usually, an octopus has eight sensitive tentacles, each of which has about 300 suckers. Each sucker on the octopus tentacle can provide corresponding suction.

The self-adhesive sanitary product of the present disclosure is designed innovatively by referring to the working principle of octopus suckers.

Figure 2:
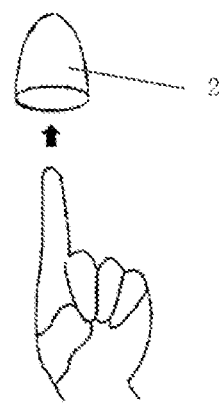
FIG. 2 is a schematic view of a self-adhesive sanitary product according to some embodiments of the present disclosure, in which a finger used to adhere the self-adhesive sanitary product to the vaginal orifice or the urethral orifice during use is additionally shown.
Figure 3:
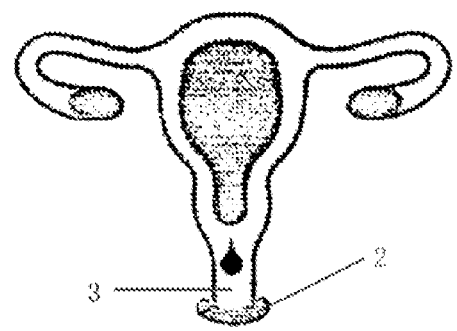
FIG. 3 is a schematic view of one of the states of the self-adhesive sanitary product in use according to some embodiments of the present disclosure.

As shown in FIG. 2, the self-adhesive sanitary product 2 of the present disclosure is in the shape of a fingerstall, one end of which is open and the other end is closed. FIG. 3 shows the female reproductive system, in which the self-adhesive sanitary product 2 of the present disclosure is adhered to the vaginal orifice 3.

The self-adhesive sanitary product 2 is designed in the shape of a fingerstall, which makes it convenient for a fingertip of a finger, such as the middle finger or the index finger as shown in FIG. 2, to be inserted into the self-adhesive sanitary product 2. Then, in the next step, the self-adhesive sanitary product 2 is gently put into the vaginal orifice with the help of the finger, and is lightly pressed by the fingertip to make it cling to the vaginal wall, and then the finger is taken out, such that the self-adhesive sanitary product 2 can be adhered to the vaginal orifice 3 or the urethral orifice (not shown). When the self-adhesive sanitary product 2 needs to be removed, it can be pulled tangentially outward to remove the adhesion.

Figure 4:
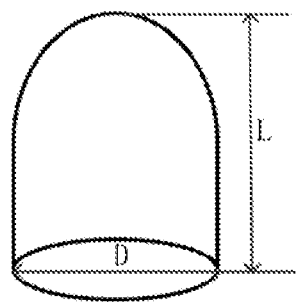
FIG. 4 is a schematic view of the self-adhesive sanitary product according to some embodiments of the present disclosure.

FIG. 4 shows a kind of dimensional design of the self-adhesive sanitary product 2. As shown in FIG. 4, a diameter D of an open end of the self-adhesive sanitary product 2 is 1.2 to 2 cm, for example, 1.5 cm. A length L of the self-adhesive sanitary product 2 is 1 to 3 cm, for example, 2 cm. In addition, a thickness of the self-adhesive sanitary product 2 is 0.1 to 0.5 mm, for example, 0.15 mm Such dimension is designed based on the sizes of most people's fingers, and other dimensions are also possible to meet different dimensional requirements. In this way, the self-adhesive sanitary product 2 is designed to be thin and tiny, so that it is convenient to store and use, and foreign body sensation during use can be avoided.

Figure 5:
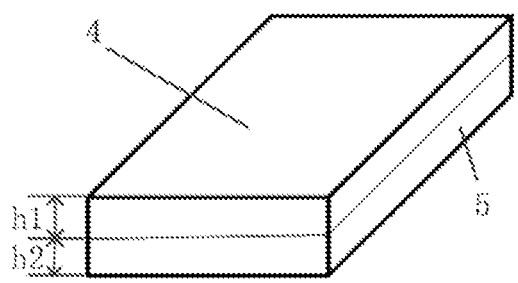
FIG. 5 is a schematic view of a base layer and a surface adhesive layer of the self-adhesive sanitary product according to some embodiments of the present disclosure.

FIG. 5 shows a section of the self-adhesive sanitary product 2 to illustrate the laminated structure of the self-adhesive sanitary product 2. As shown in FIG. 5, the self-adhesive sanitary product 2 may comprise a base layer 5 and a surface adhesive layer 4 on an upper surface of the base layer.

The base layer 5 provides mechanical support for the surface adhesive layer 4, ensuring the softness and toughness of the materials of the self-adhesive sanitary products 2. A thickness h2 of the base layer 5 may be 90 to 300 μm, for example, 100 μm.

The surface adhesive layer 4 has a micro-nano array structure on its surface that can affect reversible wet adhesion and that is configured to be adhered to the vaginal orifice. A thickness h1 of the surface adhesive layer 4 may be 10 to 200 μm, for example, 50 μm.

The self-adhesive sanitary product 2 can ensure air permeability and liquid impermeability under the condition of secure adhesion. According to some embodiments, the wet adhesion strength of the self-adhesive sanitary product 2 is 10 to 100 kPa, so that it can be adhered securely to the vaginal orifice. The thickness of the base layer 5 can be made thicker than that of the surface adhesive layer 4 to provide sufficient support. The self-adhesive sanitary product 2 of the present disclosure has a modulus of 10 to 100 kPa and a breaking stress of 1-10 MPa.

Considering the biocompatibility and degradability, the material of the base layer 5 and the surface adhesive layer 4 can respectively include sodium alginate, hyaluronic acid, carboxymethyl cellulose, xanthan gum, gellan gum, gelatin, chitosan, medical polyurethane, polyglycolic acid, polylactic acid, polylactic-glycolic acid copolymer or polycaprolactone. The above materials can be used alone or in combination. In addition, the surface adhesive layer 4 may further comprise double-network gel or fiber braided gel prepared by the combination of the above materials.

Although FIG. 5 shows that the self-adhesive sanitary product 2 comprises a base layer 5 and a surface adhesive layer 4, the self-adhesive sanitary product 2 of the present disclosure is not limited to this laminated structure. Alternatively, the self-adhesive sanitary product 2 may be integrally molded with the same material, or other layer structures may be added without affecting the use.

Figure 6:
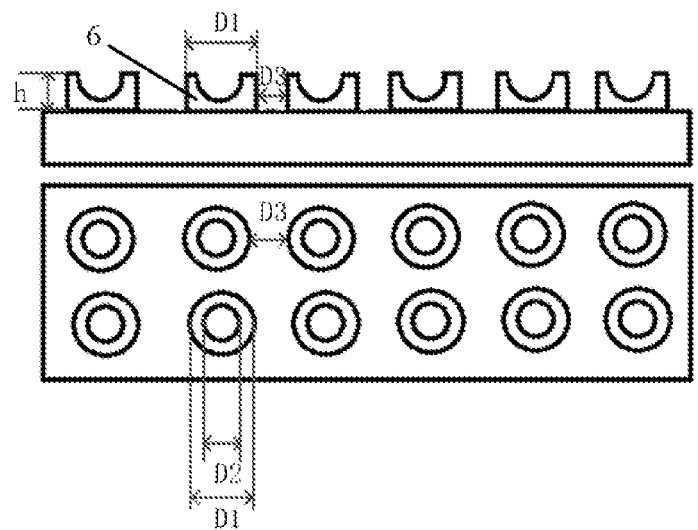
FIG. 6 is a schematic view of an octopus-like structure of the self-adhesive sanitary product according to some embodiments of the present disclosure.

The micro-nano array structure in this embodiment can be implemented as an octopus-like structure. As shown in FIG. 6, the octopus-like structure comprises a plurality of suckers 6. It should be noted that, for the purpose of illustration, FIG. 6 only shows the structure of an array of some suckers 6, and the proportion shown in FIG. 6 does not constitute a limitation on the present disclosure. An outer diameter D1 of the sucker 6 is 20 to 500 µm, for example, 100 to 200 µm, another example is 150 µm; an inner diameter D2 of the sucker 6 is 10 to 300 µm, for example, 50 to 150 µm, another example is 100 µm; and a height h of the sucker 6 is 10 to 200 µm, for example, 10 to 100 µm, another example is 50 µm. A minimum distance D3 between the outer diameters of the suckers 6 is 0.5 to 2 times of the inner diameter of the sucker 6, for example, 0.5 times, that is, D3=D2/2. If the minimum distance D3 between the outer diameters of the suckers 6 is set to be larger than the above maximum value, the density of the micro-nano array structure will be too high, and consequently the processing quality will decrease. If the minimum distance D3 between the outer diameters of the suckers 6 is set to be smaller than the above minimum value, the density of the micro-nano array structure will be too low, which will lead to poor adhesion effect.

The micro-nano array structure is spread over at least a part of the surface of the self-adhesive sanitary product 2. It is easy to understand that the spread area and the number of the micro-nano array structure are not particularly limited as long as the self-adhesive sanitary product 2 can be reliably adhered to the vaginal orifice tissue.

Second Embodiment

Based on the first embodiment, the second embodiment changes the specific structure of the sucker 6, while other parameters are the same as those of the first embodiment. Therefore, the description of the same or similar components is omitted.

Figures 7, 8:
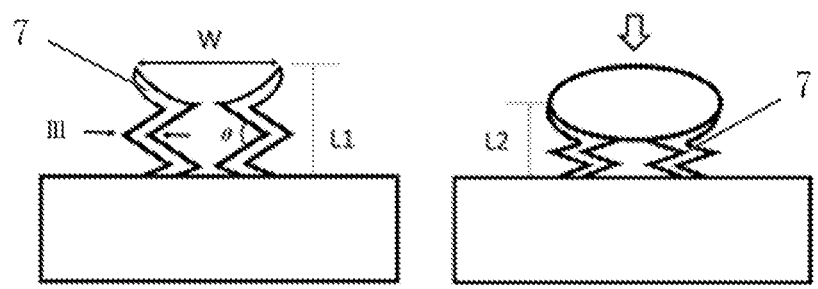
FIGS. 7 and 8 are schematic views of an elastic folding portion of the self-adhesive sanitary product according to some embodiments of the present disclosure.

As shown in FIGS. 7 and 8, a wall portion of the sucker is provided with an elastic folding portion 7 along the entire height direction, and the elastic folding portion 7 is formed by folding the wall portion of the sucker in the height direction and has elasticity similar to that of a spring. As shown in FIG. 7, in the absence of external force, the elastic folding portion 7 is in a natural stretch state. As shown in FIG. 8, the elastic folding portion 7 is compressed and folded under an external force shown by the arrow. During the transition from the natural stretch state shown in FIG. 7 to the stressed compressed state shown in FIG. 8, the air inside the elastic folding portion 7 is partially discharged, and the negative pressure formed thereby can be used to more firmly adhere the self-adhesive sanitary product to the vaginal orifice.

The specific values of the dimension and the distribution of the elastic folding portion can refer to the design values of the dimension and the distribution of the sucker structure mentioned above. Nevertheless, according to some embodiments, the dimension of the elastic folding portion in FIGS. 7 and 8 can be designed as follows:

L1=150 µm (L1 can be between 100 µm and 200 µm, and L1 is a distance between a top end and a bottom end of the elastic folding portion 7 in the natural stretch state);

L2=100 µm (L2 can be between 50 µm and 150 µm, and L2 is a distance between a top end and a bottom end of the elastic folding portion 7 in the compressed state);

W=150 µm (W can be between 100 µm and 200 µm, and W is an inner diameter of the elastic folding portion 7);

m=30 µm (m can be between 10 µm and 50 µm, and m is a wall thickness of the elastic folding portion 7); and θ=60° (θ can be between 50° and 70°, and θ is an included angle formed by the folded wall of the elastic folding portion 7 in the natural stretch state).

In the case where the sucker is not provided with the elastic folding portion, the adhesion effect brought by setting the dimension of the sucker and selecting the material of the sucker can already meet the requirement of adhering the self-adhesive sanitary product to the vaginal orifice. Further, in the case where the sucker provided with the elastic folding portion is adopted, the negative pressure generated by folding the elastic folding portion can be used to more firmly adhere the self-adhesive sanitary product to the vaginal orifice, further reducing the possibility of leakage.

In this embodiment, the elastic folding portion 7 is provided to cover the entire height of the wall portion of the sucker, but the present disclosure is not limited to this. The elastic folding portion may also be provided in a part of the height of the wall portion of the sucker.

Third Embodiment

The third embodiment changes the shape of the self-adhesive sanitary product 2 on the basis of the first embodiment and the second embodiment. Other structures and parameters are the same as those of the first embodiment and the second embodiment, so the description of the same or similar components is omitted.

In this embodiment, the self-adhesive sanitary product 2 is in the shape of a sheet. The sheet-like self-adhesive sanitary product 2 is easy to be adhered not only to the vaginal orifice, but also to the urethral orifice. Thus, the outflow of urethral contents can be blocked.

According to some embodiments, the sheet-like self-adhesive sanitary product 2 is the size of a fingernail, for example, a circle with a diameter of 0.5 cm to 2 cm. However, the dimension and the shape of the sheet-like self-adhesive sanitary product 2 are not limited and can be arbitrarily changed as long as it can be easily adhered to the vaginal orifice tissue or the urethral orifice tissue.

Fourth Embodiment

In the first to third embodiments, an octopus-like structure is taken as an example of the micro-nano array structure, but the micro-nano array structure is not limited to this. Micro-nano array structures that can achieve reversible wet adhesion and that are configured to be adhered to the vaginal orifice tissue or the urethral orifice tissue can all be applied to the present disclosure. In the fourth embodiment, other micro-nano array structures will be described. Other structures and parameters are the same as those of the first embodiment and the second embodiment, so the description of the same or similar components will be omitted. In addition, it is appreciated that a variety of micro-nano array structures that can achieve reversible wet adhesion and that are configured to be adhered to the vaginal orifice tissue or the urethral orifice tissue can be jointly arranged on the surface of the self-adhesive sanitary product 2, and work in collaboration with one another.

The micro-nano array structure may comprise a mechanical interlocking structure, which is a complementary structure in which the micro-nano array structure on the surface of the self-adhesive sanitary product 2 is fit with the tissue surface. The topological restriction at the fit part increases the separation resistance of the self-adhesive sanitary product 2 from the vaginal orifice tissue or the urethral orifice tissue, thereby enhancing the adhesion effect.

The mechanical interlocking structure can be, for example, a micro-nano array structure based on microneedles and used for skin adhesion. The mechanical interlocking structure includes, but not limited to, micro-nano array structures of microneedles based on anemone tentacle, beetle tentacle, gecko foot pad, *Parthenocissus tricuspidata* sucker, etc. and used for adhesion.

Fifth Embodiment

The fifth embodiment adds a drug-loaded slow-release layer, based on the first to fourth embodiments. Other structures and parameters are the same as those of the first to fourth embodiments, so the description of the same or similar components is omitted.

By providing a drug-loaded slow-release layer on the surface of the self-adhesive sanitary product 2, when the self-adhesive sanitary product 2 is adhered to the vaginal orifice tissue or the urethral orifice tissue, the drug is slowly released into the vagina or the urethra, so that corresponding diseases can be treated by the loaded drugs.

The drug-loaded slow-release layer can be formed by directly applying the drug on at least part of the surface of the self-adhesive sanitary product 2.

Those skilled in the art can easily understand that any of the elements in the above-mentioned first to fifth embodiments can be freely combined as long as the effects of the present disclosure can be achieved.

When the self-adhesive sanitary product 2 is adhered to the vaginal orifice tissue or the urethral orifice tissue, the self-adhesive sanitary product 2 completely blocks the vaginal orifice or the urethral orifice so as to prevent the outflow of vaginal or urethral contents, such as menstrual blood during women's menstrual period. For patients with urinary incontinence who cannot independently control urination, the self-adhesive sanitary product 2 can prevent urine from being urinated at any time. In addition, when in use, the self-adhesive sanitary product 2 is removed regularly according to the actual situation, so that menstrual blood or urine can be excreted. After removal, the self-adhesive sanitary product can be sterilized again for further use or a new self-adhesive sanitary product can be used for health needs.

Preparation Method of the Self-Adhesive Sanitary Product

The self-adhesive sanitary product of the present disclosure can be prepared by the following steps of:
(i). preparing a base layer: obtaining a sheet-like or fingerstall-like base layer film by 3D printing or electrostatic spinning or thermal pressing or ultraviolet curing;
(ii). preparing a surface adhesive layer: obtaining a sheet-like or fingerstall-like surface adhesive layer film by 3D printing or using a mold with a micro-nano array structure;
(iii). combining the surface adhesive layer with the base layer: bonding the sheet-like surface adhesive layer film with the sheet-like base layer film or boding fingerstall-like surface adhesive layer film with the fingerstall-like base layer film to obtain an interface adhesive element; and
(iv). making the interface adhesive element into a sheet shape or a fingerstall shape with a predetermined size by cutting and/or bonding.

In step (i), for example, a hydrogel fiber film can be obtained from a composite solution (pH=5-6) of chitosan (1% by mass) and sodium alginate (2% by mass) by electrospinning, or a film can be obtained by thermal pressing of pellets of biomedical polyurethane at 150-200 degrees Celsius, for example, at 180 degrees Celsius.

In step (ii), for example, a mold for obtaining the micro-nano array structure of the surface adhesive layer can be prepared by 3D printing or photolithography, and a film can be obtained by using the mold through thermal pressing or ultraviolet curing. More specifically, a mixed solution of gelatin methacryloyl (20% by mass) and sodium methacryloyl alginate (2% by mass) can be applied on the mold, and the mixed solution of gelatin methacryloyl and sodium methacryloyl alginate can be cured by ultraviolet light after air bubbles in the mixed solution are removed in vacuum. A mixture of gelatin methacryloyl and sodium methacryloyl alginate obtained by curing the mixed solution of gelatin methacryloyl and sodium methacryloyl alginate is demoulded to obtain the surface adhesive layer. Alternatively, pellets of biomedical polyurethane can be placed on a mold, heated at 150-200 degrees Celsius, for example, at 180 degrees Celsius, and applied with a pressure of 0.3-3 MPa, for example, 1 MPa, and demoulded after cooling and curing to obtain the surface adhesive layer.

In step (iv), for example, the interface adhesive element can be cut into two fingertip-like sheet materials, and then the base layers of the two fingertip-like sheet materials are adjoining to each other, and the peripheral portions of the parts except for the parts corresponding to the root of the finger are bonded together to form a fingerstall shape, or the interface adhesive element can be cut into a circular sheet with a radius of 0.5 to 2 cm.

In addition, according to the present disclosure, the self-adhesive sanitary product can also be obtained by direct molding by 3D printing. In this method, a printing ink can include gelatin methacryloyl, sodium methacryloyl alginate, gellan gum, chitosan, carboxymethyl cellulose raw materials and combinations thereof, and an aqueous solution with a concentration of 10-20% is used; and then, the printed self-adhesive sanitary product is soaked in 1 mol/L $CaCl_2$ aqueous solution for 2 hours to improve the hydrogel network and further enhance the toughness of self-adhesive sanitary product. When 3D printing is employed, generally speaking, it is more appropriate for the printing thickness to be more than 250 μm.

In addition, the preparation method of the self-adhesive sanitary product having the multi-layered structure and the fingerstall shape can refer to the method of molding a latex glove, that is, a fingerstall-like mold is first soaked into a liquid composed of the materials for preparing the surface adhesive layer, then the soaked mold leaves the liquid surface, and the surface adhesive layer is obtained by ultraviolet curing; next, the mold with the prepared surface adhesive layer is again soaked into a liquid composed of the materials for preparing the base layer, the soaked mold leaves the liquid surface, and the base layer is obtained by ultraviolet curing; and finally, demoulding is carried out to obtain the fingerstall-like self-adhesive sanitary product.

It is appreciated that only some materials are listed as examples in the above preparation methods, and those skilled in the art can choose other materials according to the actual situation and still adopt the above preparation methods.

Without departing from the spirit of the present disclosure, various technical features in the above different embodiments can be used in combination.

At present, menstrual cups, sanitary napkins, tampons or the like have their own disadvantages, respectively. The self-adhesive sanitary product provided by the present disclosure has excellent comprehensive performance in that it has the advantages of being safe, comfortable, private, miniature, environmentally friendly, affordable, etc. Therefore, the self-adhesive sanitary product provided by the present disclosure can replace the existing sanitary products used by women during menstruation, and can also be used instead of diapers by patients suffering from urinary incontinence.

(i). Technical level: Using innovative technology of materials science, a micro-nano array structure with reversible wet adhesion is prepared on the surface of the material, so that the product of the present disclosure can be safely adhered to the vaginal orifice or the urethral orifice, preventing menstrual blood leakage and urine leakage. The basic principle of the present disclosure subverts the principle of the existing menstrual sanitary products, namely absorbing or holding menstrual blood, and the principle the existing diapers, namely absorbing urine. The present disclosure can realize the minimal size, softness and comfort of the product. Biocompatible and degradable environment-friendly materials are adopted, which causes no pollution to the environment.

(ii) Application level: In appearance, the present disclosure is a miniature product, which is only the size of an index fingertip and is significantly smaller than the sizes of menstrual cups, sanitary napkins, tampons and diapers, and thus has good concealment. In addition, the micro-nano array structure with reversible wet adhesion has the characteristics of ensuring safety and no leakage, enabling the user to swim during menstruation, softness and comfort, etc. The raw materials and the processing method used in the technical solution of the present disclosure are low in cost, so the products thus manufactured are low in price and affordable.

As shown above, the present disclosure has been described in detail. For those of ordinary skill in the art, changes in the specific implementation and application scope made in line with the idea of the embodiments of the present disclosure shall not be considered as a departure from the scope of protection of the present disclosure. To sum up, the contents of this description shall not be construed as a limitation on the present disclosure.

What is claimed is:

1. A self-adhesive sanitary product, wherein
    the self-adhesive sanitary product is fingerstall-like or sheet-like, and has a first face on a surface side and a second face on an opposite side of the first face,
    the self-adhesive sanitary product, on the first face, has a micro-nano array structure configured to achieve reversible wet adhesion and configured to be adhered to a vaginal orifice tissue or a urethral orifice tissue, and
    the self-adhesive sanitary product has air permeability and liquid impermeability, and when the self-adhesive sanitary product is adhered to the vaginal orifice tissue or the urethral orifice tissue, the self-adhesive sanitary product completely blocks the vaginal orifice or the urethral orifice to prevent contents of the vagina or the urethra from flowing out.

2. The self-adhesive sanitary product according to claim 1, wherein
    the self-adhesive sanitary product comprises a base layer and a surface adhesive layer, wherein the base layer provides mechanical support for the surface adhesive layer, and the surface adhesive layer has the micro-nano array structure on the first face.

3. The self-adhesive sanitary product according to claim 1, wherein
    the micro-nano array structure comprises an octopus-like structure provided with a plurality of suckers, an outer diameter of the sucker being 20 to 500 µm, an inner diameter of the sucker being 10 to 300 µm, a height of the sucker being 10 to 200 µm, and a distance between the outer diameters of the adjacent suckers being 0.5 to 2 times of the inner diameter of the sucker.

4. The self-adhesive sanitary product according to claim 3, wherein
    the outer diameter of the sucker is 100 to 200 µm, the inner diameter of the sucker is 50 to 150 µm, and the height of the sucker is 30 to 100 µm.

5. The self-adhesive sanitary product according to claim 1, wherein
    a wet adhesion strength of the self-adhesive sanitary product is 10 to 100 kPa.

6. The self-adhesive sanitary product according to claim 1, wherein
    the fingerstall-like self-adhesive sanitary product has a thickness of 0.1 to 0.5 mm, a length of 1 to 3 cm, and an open end with a diameter of 1.2 to 2 cm; and
    the sheet-like self-adhesive sanitary product has a thickness of 0.1 to 0.5 mm, and a size that completely blocks the vaginal orifice or the urethral orifice.

7. The self-adhesive sanitary product according to claim 2, wherein
    a thickness of the base layer is 90 to 300 µm, a thickness of the surface adhesive layer is 10 to 200 µm, and the thickness of the base layer is larger than the thickness of the surface adhesive layer.

8. The self-adhesive sanitary product according to claim 1, wherein
    a modulus of the self-adhesive sanitary product is 10 to 100 kPa, and a breaking stress of the self-adhesive sanitary product is 1 to 10 MPa.

9. The self-adhesive sanitary product according to claim 1, wherein
    the first face of the self-adhesive sanitary product is provided with a drug-loaded slow-release layer, and after the self-adhesive sanitary product is adhered to the vaginal orifice tissue or the urethral orifice tissue, the drug is slowly released into the vagina or the urethra.

10. The self-adhesive sanitary product according to claim 3, wherein
at least a part of the sucker in a height direction is provided with an elastic folding portion, the elastic folding portion is in a natural stretch state without any external force and in a compressed and folded state under an external force.

11. The self-adhesive sanitary product according to claim 1, wherein
the micro-nano array structure further comprises a mechanical interlocking structure serving as a complementary structure which fits the first surface to a tissue surface of the vaginal orifice tissue or the urethral orifice tissue.

12. The self-adhesive sanitary product according to claim 1, wherein
material of the self-adhesive sanitary product includes one of, or a combination of some or all of sodium alginate, hyaluronic acid, carboxymethyl cellulose, xanthan gum, gellan gum, gelatin, chitosan, medical polyurethane, polyglycolic acid, polylactic acid, polylactic acid-ethanolic acid copolymer, or polycaprolactone.

13. A preparation method of a self-adhesive sanitary product, comprising:
preparing a base layer: obtaining a sheet-like or fingerstall-like base layer film by 3D printing or electrostatic spinning or thermal pressing or ultraviolet curing;
preparing a surface adhesive layer: obtaining a sheet-like or fingerstall-like surface adhesive layer film by 3D printing or using a mold with a micro-nano array structure;
combining the surface adhesive layer with the base layer: bonding the sheet-like surface adhesive layer film with the sheet-like base layer film or boding fingerstall-like surface adhesive layer film with the fingerstall-like base layer film to obtain an interface adhesive element; and
making the interface adhesive element into a sheet shape or a fingerstall shape with a predetermined size by cutting and/or bonding.

\* \* \* \* \*